United States Patent [19]
Boudewijn

[11] Patent Number: 5,795,322
[45] Date of Patent: Aug. 18, 1998

[54] CATHETER WITH FILTER AND THROMBUS-DISCHARGE DEVICE

[75] Inventor: Alexander C. Boudewijn, Leek, Netherlands

[73] Assignee: Cordis Corporation, Miami, Fla.

[21] Appl. No.: 629,798

[22] Filed: Apr. 9, 1996

[51] Int. Cl.⁶ ........................................ A61B 17/20
[52] U.S. Cl. ........................ 604/22; 604/27; 606/200
[58] Field of Search ................ 604/22, 27, 104–107; 606/198, 200

[56] References Cited

U.S. PATENT DOCUMENTS

| | | | |
|---|---|---|---|
| 4,723,549 | 2/1988 | Wholey et al. | 128/344 |
| 5,030,201 | 7/1991 | Palestrant | 604/22 |
| 5,053,008 | 10/1991 | Bajai | 604/104 |
| 5,193,533 | 3/1993 | Body et al. | 128/207.14 |

FOREIGN PATENT DOCUMENTS

| | | | |
|---|---|---|---|
| 0 442 579 A1 | 8/1991 | European Pat. Off. | A61M 1/00 |
| 2 606 642 | of 1988 | France | A61M 1/34 |

Primary Examiner—Corrine M. McDermott

[57] ABSTRACT

This invention relates to a catheter comprising a tube-like basic body with a distal and a proximal end, wherein the catheter comprises an expandable filter element at the distal end and a device for reducing thrombi in size and removing them. The filter element can be formed by a number of strip-shaped wall sections of the basic body defined in between longitudinal cuts evenly distributed around the circumference and may furthermore comprise a means for moving the sections of the basic body positioned on either side of the wall sections towards each other in order to make the wall sections bend outwards.

5 Claims, 1 Drawing Sheet

5,795,322

CATHETER WITH FILTER AND THROMBUS-DISCHARGE DEVICE

FIELD OF THE INVENTION

The invention relates to a catheter comprising a tube-like basic body with a distal and proximal end and wherein an expandable filter element has been arranged at the distal end. Such a catheter is introduced into a patient during surgery in order to collect thrombi and to prevent these thrombi from depositing for instance in the vascular system of the lungs and cause an embolism. The filter element of such a catheter is usually positioned in the vena cava.

The collected particles are removed or reduced in size by withdrawing the filter or by disintegrating them locally.

When removing the particles by withdrawing the catheter, there is a risk that they might come loose of the filter element and still will finish up at unwanted positions in the blood stream. Removal of the particles by allowing them to disintegrate locally can take up quite some time.

SUMMARY OF THE INVENTION

The object of the invention is to provide a catheter of the type as described in the preamble to this invention in which the drawbacks are removed.

This aim is achieved with the catheter according to the invention described herein. This invention relates to a catheter comprising a tube-like basic body with a distal and a proximal end, wherein the catheter comprises an expandable filter element at the distal end and a device for reducing thrombi in size and removing them. The filter element can be formed by a number of strip-shaped wall sections of the basic body defined in between longitudinal cuts evenly distributed around the circumference and may furthermore comprise a means for moving the sections of the basic body positioned on either side of the wall sections towards each other in order to make the wall sections bend outwards. As a result the thrombi collected by the filter element can be fragmented and removed from the body. This can be done at regular intervals or just before the catheter is removed from the body of the patient.

In a suitable embodiment, the wall sections defined in between the longitudinal cuts can bend outwards until they make contact with the wall of the blood vessel inside of which the filter element is placed. Prior to introducing the catheter, the wall sections are straightened by moving the ends of the basic body situated on either side of the wall sections away from each other. As a result the catheter will obtain a small cross-section equal to that of the basic body not provided with the longitudinal cuts, so that the catheter can be introduced with a minimum of traumatic effects.

A very suitable embodiment of the device for reducing the thrombi is size and removing them is further characterized. A stream of liquid under pressure, supplied via the pressure lumen, flows out of the jet nozzle in the form of a jet and engages sections of thrombi which are fragmented due to the energy of the jet. The thrombus fragments are conveyed by the jet to the discharge opening and removed via the discharge lumen.

Yet another very suitable embodiment of the catheter according to the invention is characterized herein. By moving the inner and outer tube-like bodies in relation to moving the inner and outer tube-like bodies in relation to one another the strip-shaped wall sections can be bent outwards or stretched respectively. On introducing the catheter, the inner tube-like body is moved as much as possible in the relatively distal direction inside the outer tube-like body, so that the strip-shaped wall sections will be stretched. After positioning the distal end of the catheter, the inner tube-like body is moved in the relatively proximal direction in the outer tube-like body, as a result of which the strip-shaped wall sections will bend outwards and consequently form the filter element. Additionally, the inner tube-like body is in that case essentially made in the form of a suction catheter, wherein all parts required for the reduction and removal device are received in this inner tube-like body.

By employing the methods of use of this device as described herein, it is ensured that the reduction and removal device can continue to work properly without getting blocked. On activating the reduction and removal device, first those parts of the thrombi extending as far as in between the bent wall sections of the filter element are engaged, after which gradually the entire structure is fragmented and removed.

Preferably the methods as set out in this invention is employed. The discharge lumen does not need to be connected in that case to a separate source of suction. As a result of the ejector action a sufficient flow is maintained in the discharge lumen without applying additional suction.

DESCRIPTION OF THE DRAWINGS

The invention will be explained in greater detail in the following description with reference to the attached drawings.

DETAILED DESCRIPTION OF THE INVENTION

Figure 1:
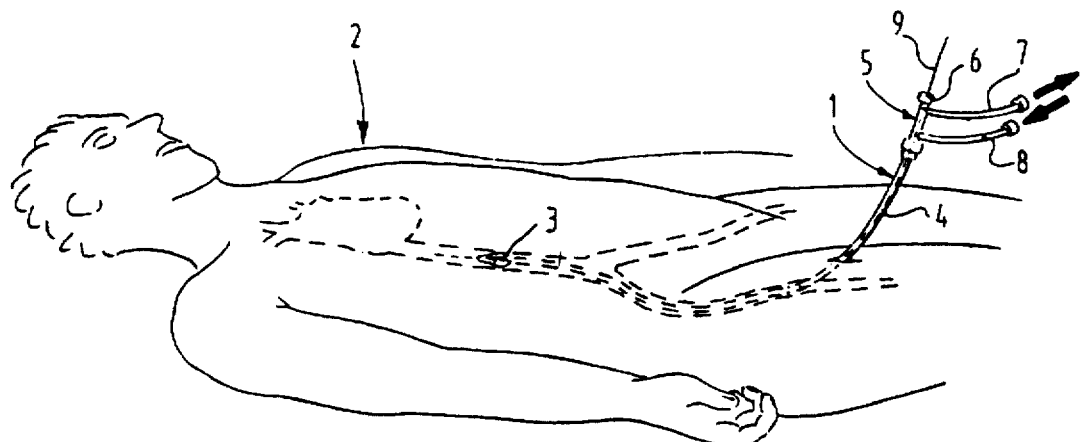
FIG. 1 shows schematically the application of a catheter according to the invention.

As is illustrated schematically in FIG. 1, a catheter 1 according to the invention is introduced into a patient 2, in order to position a filter element 3 at the distal end of the catheter 1 inside a blood vessel, in particular in the vena cava.

The catheter 1 comprises a tube-like basic body 4 with a filter element 3, still to be explained in greater detail, at the distal end and a connecting member 5 at the proximal end.

The connecting member 5 comprises in this example of an embodiment a haemostatic valve 6 through which a guide wire 9 is advanced, which is employed in the usual manner for the purpose of positioning the catheter 1.

Furthermore the connecting member 5 comprises a discharge connection 7 which is connected with the discharge lumen in the basic body 4 and a pressure connection 8 which is connected with a pressure lumen in the basic body 4.

The basic body 4 of the catheter 1 comprises an outer tube-like body 13 and an inner tube-like body 14 received therein in a, in a longitudinal direction, movable manner. The outer tube-like body 13 and the inner tube-like body 14 are connected to each other with their distal ends. At the very end, a tip 17, made of a soft material, has been arranged in order to prevent trauma on introduction of the catheter 1 into the blood vessel 12.

Figure 3:
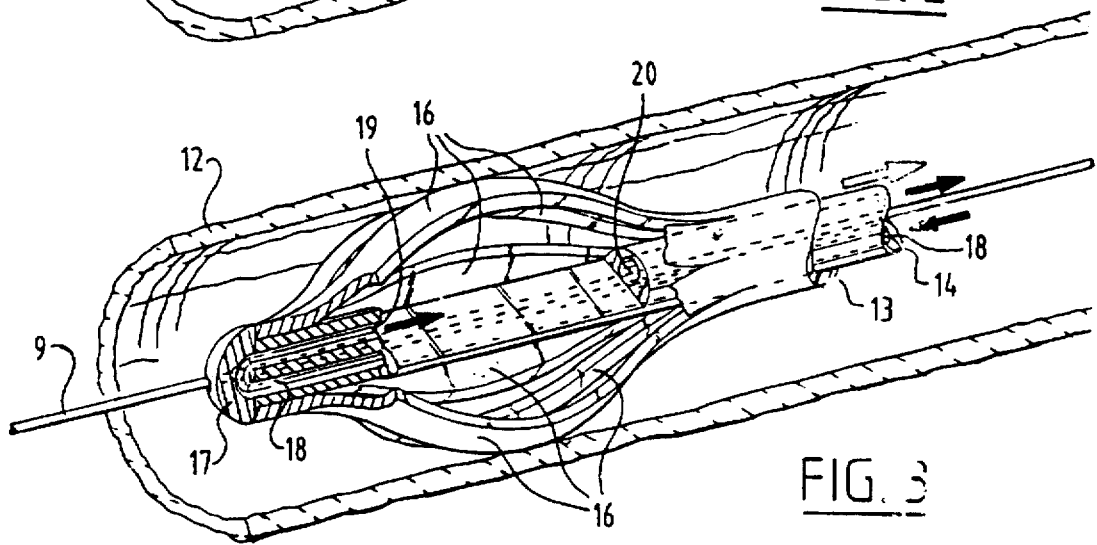
FIG. 3 shows a view corresponding to that of FIG. 2 in which case the filter element is illustrated in working state.

At the distal end of the outer tube-like body 13, a number of longitudinal cuts 15, distributed evenly around the circumference, have been arranged defining strip-shaped wall sections 16 in between them. The wall sections 16 together form the actual filter element. By pulling the inner tube-like body 14 at the proximal end of the catheter 1 over a limited distance in relation to the outer tube-like body 13 outwards, the stripshaped wall sections are put under a compression load in a longitudinal direction as a result of which they will bend outwards in the direction illustrated in FIG. 3. The relative displacement of the outer tube-like body and the inner tube-like body is chosen is such a manner, that the wall sections 16 make a good contact with the inner wall of the blood vessel 12.

It will be clear that thrombi as from a certain size, flowing through the blood vessel 12, will be collected by the filter element formed by the wall sections 16 bending outwards, and that at the same time the blood can flow in a normal manner through these wall sections.

The inner tube-like body 14 comprises the aforementioned pressure lumen 18 connected with the pressure connection 8. In the manner illustrated if FIG. 3, the pressure lumen 18 is connected with a channel section extending backwards in proximal direction forming a jet nozzle 19. The jet nozzle 19 is directed at a discharge opening 20 which forms the end section of a discharge lumen in the inner tube-like body 14, which is connected in the above described manner with the discharge connection 7.

In addition to the pressure lumen and the discharge lumen, the inner tube-like body 14 comprises another lumen for the guide wire 9.

End sections of thrombi collected by the filter element will extend as far as inside the space defined by the wall sections 16 bending outwards. In order to reduce the thrombi in size and remove them, liquid under pressure is supplied to the pressure connection 8, so that a powerful liquid jet leaves the pressure nozzle 19 in the direction of the discharge opening 20. The end sections of the thrombi are engaged by this liquid jet and reduced in size by mechanical action and entrained through the discharge opening 20 in the discharge lumen. In order to stimulate the discharge flow, a vacuum source can be connected to the discharge connection 7. As a result of the suction action, the thrombi are gradually sucked further into the space defined by the wall sections 16 where they are gradually reduced in size and ultimately removed via the discharge lumen.

The jet nozzle 19 and the discharge opening 20 can, in a suitable manner, be arranged and dimensioned in relation to each other in such a way that the flow of liquid leaving the jet nozzle 19 creates an ejector-action as a result of which a separate flow is created in the discharge lumen towards the proximal end without additional suction action at the discharge connection 7.

It will be clear that the thrombi reduction and discharge device, and the filter element likewise, can be embodied in different ways. The reduction and discharge device may for instance comprise several (for instance two) jet nozzles with corresponding discharge openings. It will also be possible to arrange the reduction and discharge device at for instance the relatively distal end of the filter element, that is to say outside the spaced defined by the wall sections bending outwards. Another possibility is a combination of a reduction and discharge device both in and outside the filter element.

Figure 2:
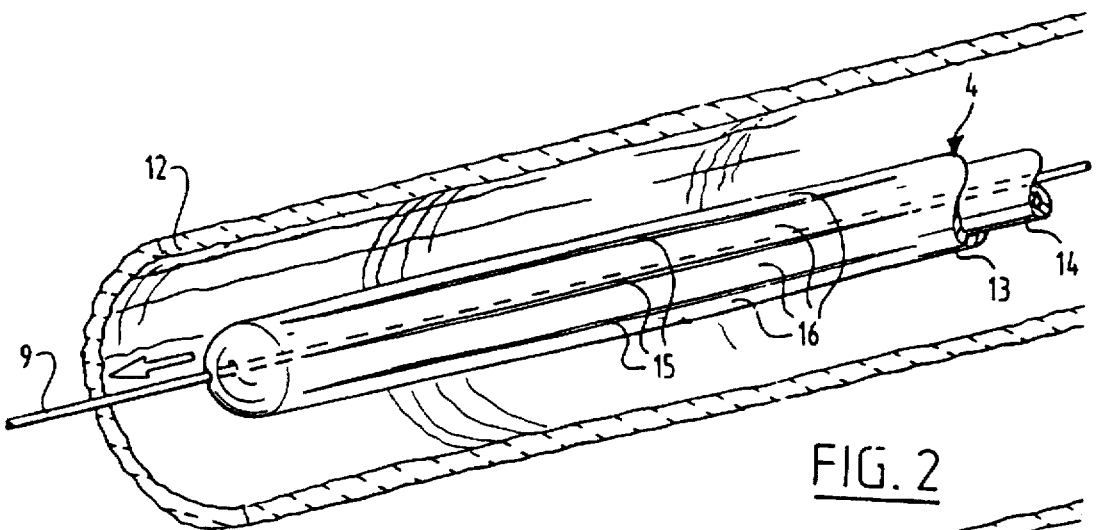
FIG. 2 illustrates the distal end of a catheter according to the invention when being positioned in the blood vessel.

When the filter catheter has carried out its task, and there is no longer a danger for the patient of an embolism forming, the catheter can be removed. In order to achieve this, the inner tube-like body is moved in relation to the outer tube-like body in a relatively distal direction, so that the wall sections 16 bending outwards are stretched again into the state illustrated in FIG. 2. The catheter will then have resumed its original small cross-section, so that it can be withdrawn easily.

I claim:

1. Catheter comprising:

a tube-like catheter body with a distal and a proximal end connected by a longitudinal section, wherein the catheter comprises at the distal end an expandable filter element; and further contained at the distal end, a device for reducing thrombi in size and removing them; and wherein the filter element is formed by a number of strip-shaped wall sections of of the tube-like catheter body defined in between longitudinal cuts evenly distributed around the circumference; and furthermore comprising a means for moving sections of the tube-like catheter body, said means for moving situated on the distal end and causing certain of the wall sections to move towards each other in order to make other parts of the wall sections bend outwards; and wherein the device for reducing thrombi comprises a jet nozzle connected to a pressure lumen and a discharge opening connected to a discharge lumen, said device situated inside the tube-like catheter body such that said jet nozzle is pointing in the proximal direction and said discharge opening is proximal of said jet nozzle.

2. Catheter as claimed in claim 1 comprising an outer tube-like body and an inner tube-like body received inside it in a movable manner, which are connected to each other at their digital ends and wherein the strip-shaped wall sections have been formed in the outer tube-like body.

3. Catheter as claimed in claim 1 wherein the jet nozzle has been positioned and dimensioned in relation to the discharge opening in such a way that they form an ejector.

4. Catheter comprising:

a tube-like catheter body with a distal and a proximal end connected by a longitudinal section, wherein the catheter comprises at the distal end an expandable filter element; and further contained at the distal end, a device for reducing thrombi in size and removing them; and wherein the filter element is formed by a number of strip-shaped wall sections of the tube-like catheter body defined in between longitudinal cuts evenly distributed around the circumference; and furthermore comprising a means for moving sections of the tube-like catheter body, said means for moving situated on the distal end and causing certain of the wall sections to move towards each other in order to make other parts of the wall sections bend outwards; and wherein the device for reducing thrombi comprises a jet nozzle connected to a pressure lumen and a discharge opening connected to a discharge lumen, said device situated inside the tube-like catheter body such that said jet nozzle is pointing in the proximal direction and said discharge opening is proximal of said jet nozzle; and wherein the pressure lumen and the discharge lumen are received inside the tube-like catheter body.

5. Catheter as claimed in claim 4, wherein the jet nozzle and the discharge opening are positioned inside the longitudinal section of the catheter body, wherein the longitudinal cuts extend.

* * * * *

UNITED STATES PATENT AND TRADEMARK OFFICE
CERTIFICATE OF CORRECTION

PATENT NO. : 5,795,322
DATED : August 18, 1998
INVENTOR(S) : Alexander C. Boudewijn It is certified that error appears in the above-identified patent and that said Letters Patent is hereby corrected as shown below:

On the title page, insert item [30], Foreign Application Priority Data
  --Apr. 10, 1995 [NL] Netherlands............................... 1000105--

Signed and Sealed this

Sixteenth Day of March, 1999

Attest:

Q. TODD DICKINSON

*Attesting Officer*  *Acting Commissioner of Patents and Trademarks*